United States Patent [19]
Hearst et al.

[11] Patent Number: 5,637,759
[45] Date of Patent: Jun. 10, 1997

[54] METAL-LIGATING AMINO ACID DERIVATIVES FOR MRI AND FOR PEPTIDE SYNTHESIS

[75] Inventors: John E. Hearst, Berkeley; Tariq M. Rana; Matt Ban, both of San Francisco, all of Calif.

[73] Assignee: The Regents of the University of California, Oakland, Calif.

[21] Appl. No.: 923,226

[22] Filed: Jul. 30, 1992

[51] Int. Cl.⁶ .................................................. C07C 261/00
[52] U.S. Cl. .............................. 560/159; 534/16; 556/50; 556/63; 556/116; 556/134; 556/148; 560/24; 560/32; 560/33; 562/433; 562/450; 562/465
[58] Field of Search ........................... 560/159, 24, 32, 560/33; 562/450, 433, 465; 556/50, 63, 116, 134, 148, 1; 534/16

[56] References Cited

U.S. PATENT DOCUMENTS 4,647,447  3/1987  Gries .................................. 424/9

Primary Examiner—Michael L. Shippen
Attorney, Agent, or Firm—Peters, Verny, Jones & Biksa, L.L.P.

[57] ABSTRACT

Novel organic compounds and metal ion-containing amino acid chelates are described which are useful in solid phase synthesis of polypeptides and as magnetic resonance imaging (MRI) enhancing agents. The present invention also relates to a convenient and straightforward method to synthesize a metal-ligating amino acid suitable as MRI enhancing agents or for introducing a strong metal binding site at any chosen position in a peptide. Some compounds are designed to be compatible with N-α-Fmoc peptide synthesis strategy, and can easily be prepared on large scale. Thus, flexible linkers of different lengths and containing various structures can be placed between the α-carbon backbone of peptides and metal binding moieties. These peptides will provide a variety of affinity cleaving reagents which can be directed against protein or nucleic acid targets. Therefore, these molecules can serve as an important tool to study protein folding, protein-protein and protein-nucleic acid interactions.

13 Claims, 1 Drawing Sheet

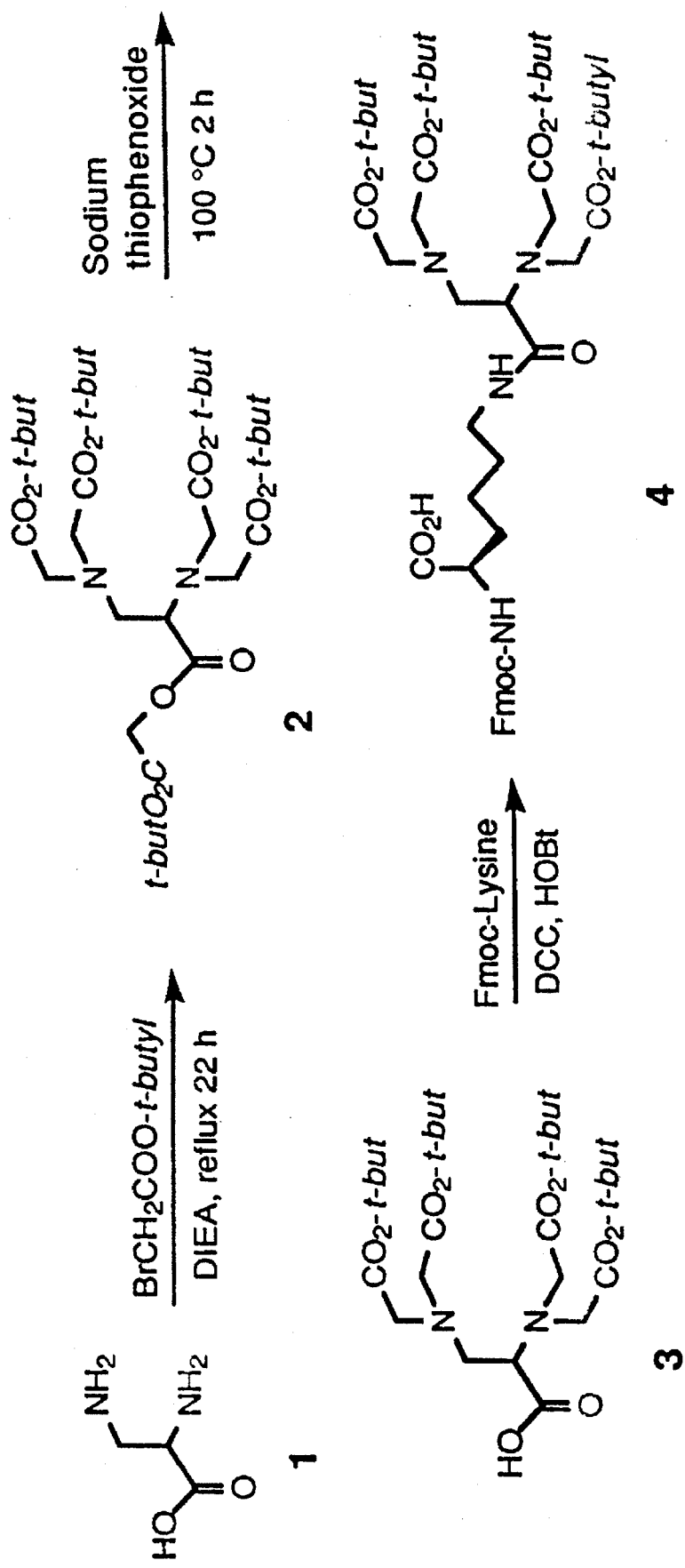
FIG._1

METAL-LIGATING AMINO ACID DERIVATIVES FOR MRI AND FOR PEPTIDE SYNTHESIS

ORIGIN OF THE INVENTION

The present invention was made in part in research supported by the United States National Institutes of Health Grant # FD 8RI GM 41911A-03-NF-A-03/92. The U.S. Government has rights in this invention.

BACKGROUND OF THE INVENTION

1. Field of the Invention

The present invention relates to novel metal-ligand amino acid derivatives which are useful as Magnetic Resonance Imaging (MRI) agents or as compounds useful to incorporate a metal ion containing-chelate amino acid derivative at any point in a polypeptide during conventional solid phase synthesis of a polypeptide.

2. Description of the Related Art

MRI contrast enhancing agents

The utility of magnetic resonance imaging (MRI) also known as nuclear magnetic resonance (NMR) imaging in diagnostic medicine has recently been improved by the development of pharmaceutical MRI contrast agents which change the relaxation times of water protons in the vicinity of the agent. A pharmaceutical MRI contrast agent is selected to bind to a component of a body tissue under study, thereby increasing the relaxivity of water protons in the vicinity of the tissue to which the agent is bound. Thus, the MRI signal from the tissues of interest is enhanced relative to the surrounding tissues. MRI contrast image enhancing agents incorporate organic groups into metal chelating ligands to produce metal ion-chelate MRI contrast enhancing agents which preferentially bind to specific proteins in a non-covalent and non-immunologic manner. As a result of this binding the protons of the water molecules in the vicinity of the metal ion chelates have a relaxivity that is enhanced by at least a factor of two or more relative to the relaxivity induced by the paramagnetic complex free in solution.

Tissue specificity of MRI contrast agents is due in part to the structure of the metal ion chelate and its ability to mimic the structure of naturally occurring molecules which have an affinity for the tissue of interest (e.g. liver, gall bladder intestine, heart). Further, the binding of the metal ion chelates to such tissues is sometimes enhanced by the incorporation of substituents which increase the lipophilicity and hydrophobicity of specific portions of the molecule.

Some of the metal ion chelates mimic the structure of bilirubin and thereby exhibit preferential binding to albumin, to the hepatocellular uptake protein, to ligandin, and to the fatty acid binding proteins. The ability of the organic chelates to bind to these proteins renders them useful in enhancing the image of normal liver tissue on the presence of tumors, for monitoring liver function, and for enhancing the image of the bile ducts and gall bladder. In addition, binding to albumin in the blood creates a high relaxivity blood-pool contrast agent that is useful in detecting disruption of the blood-brain barrier, in MRI angiography, in perfusion imaging, and in distinguishing between tumors and blood-filled lesions such as hemangiomas and hemorrhage.

Some references of interest in the synthesis and of these novel amino acid derivatives useful as MRI contrast enhancing agents are as follows:

H. Gries, et al., U.S. Pat. No. 4,647,447.

S. C. Quay, U.S. Pat. No. 4,637,929.

R. B. Lauffer, PCT/US90/04887 (WO 91/03200) 21 Mar. 1991.

B. Engelstad, et al., U.S. Pat. No. 4,972,837.

D. L. White, et al., U.S. Pat. No. 4,999,445.

D. D. Stark and W. G. Bradley, Jr., *Magnetic Resonance Imaging*, C. V. Mosby Co., Washington, D.C. 1988.

F. E. Armitage, et al. *Bioconjugate Chem.* 1990, Vol. 1, pp. 365–375.

Metal Containing Chelates Containing Amino Acid Derivatives For Polypeptide Synthesis Some references about the synthesis of metal containing chelates containing amino acid derivatives follow. These references are referred to by number in the following text.

1. H. E. Moser, et al. *Science* (Washington, D.C.) 1987, Vol. 238, 645–650. 1(b). M. G. Oakley, et al. *Science* (Washington, D.C.) 1990, Vol. 248, 847–850. 1(c). J. A. Latham, et al. *Science* (Washington, D.C.) 1989, Vol. 245, 276–282. 1(d). H. Y. Mei, et al. *Proc. Natl. Acad. Sci. USA* 1988, Vol. 85, 1339–1343. 1(e). C. B. Chen, et al. *Science* (Washington, D.C.) 1987, Vol. 237, 1197–1201. 1 (f). T. D. Tullius, et al. *Proc. Natl. Acad. Sci. USA* 1986, Vol. 83, 5469–5473.

2.(a) T. M. Rana, et al. *J. Am. Chem. Soc.* 1991, Vol. 113, 1859–1861. 2(b). T. M. Rana, et al. *J. Am. Chem. Soc.* 1990, Vol. 112, 2457–2458.

3.(a) Schepartz, A., et al. *J. Am. Chem. Soc.* 1990, Vol. 112, 3247–3249. 3(b). D. Hoyer, et al. *J. Am. Chem. Soc.* 1990, Vol. 112, 3249–3250.

4. T. M. Rana, et al. *Proc. Natl. Acad. Sci. USA* 1991, Vol. 88, 10578–10582.

5.(a) C. F. Meares, *European Journal of Solid State and Inorganic Chemistry* 1991, Vol. 28, S:223. 5(b). D. A. Cope, et al. *Cancer Research* 1990, Vol. 50, 1803–1809. 5(c). J. A. Williams, et al. *Cancer Research* 1990, Vol. 50 (3 Suppl.), 974s–979s. 5(d). A. R. Fritzberg, et al. *Pharmaceutical Research* 1988, Vol. 5, 325–334.

6.(a) J. P. Sluka, et al. *Science* 1987, Vol. 238, 1129–1132. 6(b). J. P. Sluka, et alo *J. Am. Chem. Soc.* 1990, Vol. 112, 6369–6374.

7. R. Arya, et al. *J. Bioconjugate Chem.* 1991, Vol. 2, 323–326.

8. B. Cuenoud, et al. *Tetrahderon* 1991, Vol. 47, 2535–2542.

9. R. B. Merrifield, *Adv. Enzymol* 1969, Vol. 32, 221–298.

10. G. B. Fields, et al. *Int. J. Peptide Protein Res.* 1990, Vol. 35, 161–214.

11.(a) J. C. Sheehan, et al. *J. Org. Chem* 1964, Vol. 29, 2006–2008. 11(b). G. C. Stelakatos, et al. *J. Chem. Soc.* 1966, C, pp. 1191–1199.

12. S. S. Isied, et al. *J. Am. Chem. Soc.* 1982, Vol. 104. 3910–3916.

13. E. Atherton, et al. *J. Chem. Soc. Chem. Com.* 1978, p. 537, and 539.

14. L. A. Carpino, et al. *J. Org. Chem.* 1972, Vol. 37, 3404.

All references, patents, articles, standards, and the like cited in this application are hereby incorporated by reference in their entirety.

The cleavage of DNA or RNA by metal chelates is an important new approach to characterize specific structural features of nucleic acids and their complexes in solution. (Ref. 1). Recently, there has been considerable interest in the cleavage of proteins by metal ions or chelates bound at particular sites. (Ref. 2 and 3). Site-specific cleavage of proteins is often achieved by introducing a metal-binding site at one position in a polypeptide chain. (Ref. 2). A reaction has been reported in which proteins are hydrolyzed by an analog of iron-EDTA in the presence of ascorbate and hydrogen peroxide. (Ref. 4). Inducing proteolysis with metal ion-containing chelates would permit mapping a site of interest by determining which individual peptide bonds are close to the metal site. Another important use of a metal-containing chelator is to prepare radiolabeled monoclonal antibodies for the early detection and therapy of cancer. (Ref. 5). Syntheses of peptides carrying EDTA at N-terminus or proximal to C-terminus have been reported. (Ref. 6 and 7). An EDTA analog of N-α-Boc-lysine amino acid has been recently synthesized. (Ref. 8). With one exception (Ref. 7), all synthetic routes utilize one of the carboxylic acid arms of the EDTA as a "handle" to covalently anchor the chelating site to the peptides.

This approach methodology of the art has at least two limitations:

(i) the metal binding moiety is not exactly that of EDTA and affinity cleavage of proteins using this chelate (ethylenediaminetriacetic acid) results in non-hydrolytic fragments, (Ref. 3), and (ii) stability of metal complexes may be a problem during the use of the chelate to prepare radiopharmaceuticals.

N-α-Tert-butyloxycarbonyl-(Boc) protected amino acids are used for Merrifield solid phase peptide synthesis. (Ref. 9). However, there are two major concerns about this synthetic strategy:

(a) repetitive TFA acidolysis in Boc-group deprotection could lead to acid catalyzed side-reactions, and (b) cleavage and deprotection of peptides requires HF and specific laboratory set up which is not available to many researchers. Due to these concerns Fmoc (9-fluorenylmethylcarbamate) solid phase peptide synthesis was developed which employs N-α-Fmoc amino acid (Ref. 10). In this polypeptide approach, the Fmoc group is deprotected with piperidine and trifluoroacetic acid (TFA) is required only for the final cleavage and deprotection step. Compound 4 of this invention was designed to be compatible with the Fmoc solid phase peptide synthesis strategy.

It would be useful to have additional, novel metal organic ligands and metal chelates for research and/or diagnostic uses. The present invention provides a simple and straight-forward synthesis of a modified amino acid (e.g. lysine-compound (4) for incorporation of metal-ligating functionality (e.g. ethylenediaminetetraacetic acid) at any desired position in a peptide. The compounds of this invention are also useful as MRI contrast enhancing agents.

SUMMARY OF THE INVENTION

The present invention relates to an amino acid-chelate as a magnetic resonance imaging agent or for use in solid phase synthesis of polypeptides which has the structure:

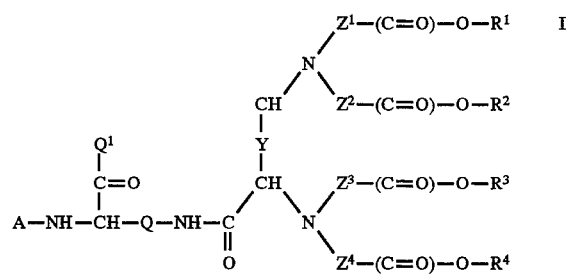

wherein Y is a direct bond,

A is an amine protecting group provided that it is not t-Boc;

Q is selected from a straight chain alkylene, branched chain alkylene, or alicyclic alkylene having 1 to 10 carbon atoms, phenylene,

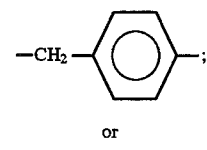

or

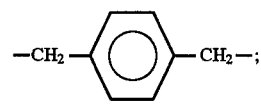

$Q^1$ is independently selected from —OH, $OCH_3$, $OCH_2CH_3$, O-phenyl, O-benzyl, $NH_2$, $NHCH_3$, $NHCH_2CH_3N(CH_3)_2$, or $N(CH_2CH_3)_2$.

$Z^1$, $Z^2$, $Z^3$ and $Z^4$ are each independently selected from —$CH_2$—, —$CH_2CH_2$—, —$CH_2$—$CH(CH_3)$—$CH_2$—, or —$CH_2CH_2CH_2CH_2$—;

$R^1$, $R^2$ $R^3$, and $R^4$ are each independently selected from —H, —$C(CH_3)_3$ or when $R^1$, $R^2$, $R^3$, and $R_4$ are in ion form they coordinate as bonds to a metal ion M wherein M is independently selected from transition metals having an atomic number of between 21 and 29, or 30, 31, 39, 40, 43, 48, 49, or lanthanide metals having an atomic number of between 57 and 71 or 80, 81 or 82; and when Y is

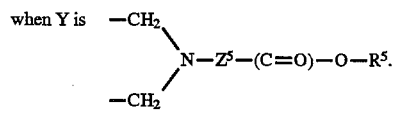

A is an amine protecting group selected from Fmoc or other protecting groups provided that it is not t-Boc;

$Z^5$ is independently selected from $Z^1$ and $R^5$ is independently selected from $R^1$ or when in ion form $R^1$, $R^2$, $R^3$, $R^4$, and $R^5$ coordinate a metal ion M as shown M and defined hereinabove.

In another aspect, the present invention relates to a process for the manufacture of the amino acid-chelate of structure I wherein $R^1$, $R^2$, $R^3$, $R^4$, and optionally $R^5$ are each —$C(CH_3)_3$, which process comprises:

(A) contacting a compound of the structure:

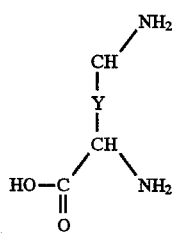     II wherein Y is in a direct bond or —CH$_2$NHCH$_2$— with sufficient compound of the structure X—Z$^1$—(C=O)OC(CH$_3$)$_3$, wherein X is halogen selected from chloro, bromo or iodo, and Z$^1$ is selected from —CH$_2$— or —CH$_2$CH$_2$— to react with all —NH bonds present in sufficient dipolar aprotic solvent to cause dissolution of II and in the presence of a tertiary alkyl amine;

(B) refluxing the reaction mixture of step (A) for between about 5 and 48 hr followed by cooling to ambient temperature and removing the solvent under vacuum producing crude compound III;

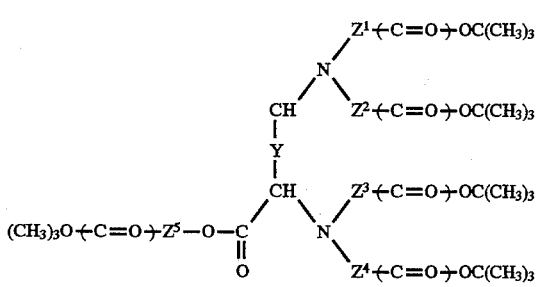     III and Z$^5$ is defined above;

(C) contacting the product remaining in step (B) with an anhydrous water-immiscible oxygenated alkyl containing solvent with stirring to redissolve the product;

(D) separating and drying the water immiscible organic phase, adding a polar aprotic water immiscible solvent;

(E) washing the organic phase with an aqueous buffer having a pH of between about 1 and 4;

(F) separating the organic phase and aqueous phase;

(G) drying the organic phase and removing the solvent in vacuum producing a purified polyaminepolyester having multiple —C(CH$_3$)$_3$ ester groups of structure III;

(H) dissolving the product of step (G) in sufficient dimethylformamide, diethylformamide, hexamethylphosphoramide, tetramethylenesulfone, dimethylsulfoxide or mixtures thereof adding sodium thiophenoxide to produce Compound III wherein Q$^1$ is OH;

(I) heating to between about 90° and 110° C. for between about 0.5 and 6 hr, cooling to ambient temperature with dilution using a volume equivalent of a polar aprotic water-immiscible hydrocarbon solvent;

(J) contacting the organic solution of step (I) with aqueous buffer having a pH between about 1 and 4, separating the organic layer and removing the solvent under vacuum;

(K) purifying the product of step (J) by column chromatography using an eluent of increasing polarity of a mixture of n-hexane and ethyl acetate followed by a weak organic acid in an organic alkyl ester;

(L) contacting the product of step (K), the polybutyl ester protected polyfunctional chelating agent; with a chlorinated hydrocarbon solvent and a carbonyl group activator selected from 1-hydroxybenzotriazole, HBTU, TBTU, or BOP, contacting at 0° C. the solution of step (K) with a peptide coupling agent selected from carbodiimide, DCC, or CDI or EDC, followed by filtration, and evaporating the filtrate in vacuum;

(M) contacting with stirring the activated ester of step (L) with excess compound of structure IV:

N-α-Fmoc-NH—CH—(COOH)—Q—NH$_2$     IV at ambient temperature for between 6 and 48 hr in oxygenated organic water immiscible liquid and a tertiary alkyl amine to adjust the pH of the reaction to between about 7 and 9, followed by removal of the solvent in vacuum;

(N) dissolving the product of step (M) in an organic ester to remove excess protected amino acid in the presence of a weak organic polyacid, drying the solution and removal of the solvent under reduced pressure;

(O) purifying the crude product of step (N) using reverse phase; chromatography producing the amino acid-chelate of structure I.

In another aspect, the present invention also relates to the use of the metal ion amino acid-chelate for use as an MRI enhancing agent and in a solid phase peptide synthesis to insert an amino acid-chelate capable of introducing a strong metal binding site at any amino acid position in a synthetic peptide.

The present invention also relates to a process to produce a metal ion containing polypeptide which process comprises (h) contacting the polypeptide chelate produced herein with aqueous buffer at pH 6 to 8 at ambient temperature adding aqueous metal M salts to produce the metal ion chelate and isolating the metal ion chelate.

The present invention also concerns the use of the amino acid-chelate as found in the Summary (supra), for use as on MRI enhancing agent or for use in a solid phase peptide synthesis to insert an amino acid ligand—or metal ion chelate capable of introducing a strong metal binding site at any position of synthetic polypeptide.

BRIEF DESCRIPTION OF THE FIGURES

FIG. 1 is a reaction sequence for preparing the chelate-amino acid derivative useful in peptide synthesis.

DETAILED DESCRIPTION OF THE INVENTION AND PREFERRED EMBODIMENTS

Definitions:

As defined herein,

"Alkylene" refers to a methylene —CH$_2$—, ethylene, propylene, and the like up to 10 carbon atoms.

"DPTA" refers to diethylenetriaminepentacetic acid.

"EDTA" refers to ethylenediaminetetraacetic acid.

"BOP" refers to Castro's Reagent—Benzotriazole-1-yl-oxy-tris-(dimethylamino)-phosphonium hexafluorophosphate.

"CDI" refers to 1,1'-Carbonyldiimidazole.

"DCC" refers to N,N'-Dicyclohexylcarbodiimide.

"DIC" refers to N,N'-Diisopropylcarbodilmide.

"EDC" refers to 1-Ethyl-3-(3-Dimethylaminopropyl)-carbodiimide.

"HBTU" refers to 2-(1H-Benzotriazol-1-yl)-1,1,3,3-tetramethyluronium hexafluorophosphate.

"HOBT" refers to N-Hydroxybenzotriazole.

"HONB" refers to N-Hydroxy-5-norbornene-2,3-dicarboximde.

"Metals of atomic number 21 to 29" refers to scandium titanium, vanadium, chromium, manganese, iron, cobalt, nickel, copper, zinc and gallium respectively. Paramagnetic ions are more preferred. Iron, manganese, nickel, chromium, cobalt are especially preferred.

"Metals (lanthanides) having an atomic number from 57 to 71" refers to lanthanide, cerium, praseodymium, etc. to lutentium, respectively. Paramagnetic gadolinium (III) or dysprosium (III) are preferred.

"PyBROP®" refers to Bromo-tris-pyrrolidino-phosphonium hexafluorophosphate.

"PyBOP®" refers to Benzotriazole-1-yl-oxy-tris-pyrrolidino-phosphonium-hexafluorophosphate.

"TBTU" 2-(1H-Benzotriazol-1-yl)-1,1,2,2-tetramethyluronium tetrafluoroborate.

The value of the ligand of structure I of the present invention is that, in effect, more carboxyl groups are available to coordinate metal ion M, than with presently available comparable structures of the art.

MRI Agents:

The contrast agents of this invention localize in several organ systems, e.g., in the kidney, urinary tract, and urinary bladder; in the liver biliary tree, and intestinal lumen; and in the myocardium of the heart. This localization results in increased MRI signal and image contrast. The resulting images show both improved anatomic detail and allow the functional state of certain organ systems, e.g., the urinary and biliary systems, to be ascertained.

This localization probably involves a combination of physio-chemical and receptor-based mechanisms. For example, binding to blood components results in enhancement of the blood pool and may contribute to heart enhancement. Localization in the liver may result from recognition and transport by hepatocytes. Other mechanisms may also be involved. It is possible to target other organs and tissues by selective modification of the structure of the chelate.

In preferred embodiments for MRI agents A is independently selected from $A^1$ or $A^2$ wherein $A^1$ for MRI agents are independently selected from C1–C10 alkly, aryl, alkylenearyl, substituted aryl or alkylene substituted aryl. Aryl is phenyl or naphthyl. Aryl may be substituted with one to three groups independently selected from chloro, bromo, iodo, hydroxy, alkoxyl or trifluoromethyl and $A^2$ is defined herein.

Solid Phase Peptide Synthesis Reagents Synthesis Of The Organic Ligand and Metal Ion Chelates The synthesis of the novel organic ligand and metal ion chelate is as described below:

Step A

The diaminocarboxylic acid (e.g. Compound II or Compound 1) is dissolved in excess dipolar aprotic solvent with 5 or more equivalents of tert-butyl halogen acetate (e.g., chloro or bromo or iodo) and 5 or more equivalents of a tertiary alkyl amine. Dipolaf aprotic solvents include, for example acetonitrile, butyrylnitrile, methylethylketone, tetramethylenesulfone, dimethylformamide, dimethylsulfoxide and the like. Alkyl nitriles are preferred, especially acetonitrile. Tertiary alkyl amines include, for example, trimethylamine, triethyl amine, triisopropylamine, diisopropylmethyl amine, disopropylethylamine, and the like. The tertiary amine is present to produce a salt with the released halogen ion.

Step B

The solution of step A is heated to between about 100° to 150° C. (to reflux for nitriles, e.g., acetonitrile) for between about 5 and 48 hr followed by cooling to ambient and removal of the solvent. For a nitrile solvent, the reaction mixture is generally refluxed for between about 20 and 24 hr, cooled and the nitrile (e.g., acetonitrile) is removed under reduced pressure.

Step C

The residue product of step B is contacted (triturated) with an aprotic organic solvent stirred for about 5 to 48 hr at ambient temperature and pressure and filtered. Anhydrous oxygenated alkyl containing solvents are preferred, especially alkyl ethers, such as dimethyl ether and the like. A preferable time for stirring is about 20 to 24 hr.

Step D

The water-immiscible organic phase of step C is separated from any solid, (e.g. by filtration) and dried (e.g. using a solid drying agent or molecular sieves). Next the organic phase is separated from the drying agent and combined with one-half to a 3-fold excess by volume of a dipolar organic solvent (e.g. toluene).

Step E

The organic phase is washed 3 to 10 times with about an equal volume of aqueous buffer at a concentration about 0.1M having a pH of about 1 to 4, especially about 2.

Step F

The organic phase is separated from the aqueous phase.

Step G

The organic phase is dried using a conventional drying agent (e.g., anhydrous magnesium sulfate or sodium sulfate or molecular sieves) and removing the organic solvents present under reduced pressure producing the purified polyamine polyester having multiple t-butyl ester groups of structure III.

Step H

The solid product of step G (e.g. compound 2) was dissolved in sufficient dipolar aprotic solvent. Preferred dipolar aprotic solvents include for example dimethylformamide, diethylformamide, hexamethylphosphoramide, tetramethylenesulfone, dimethylsulfoxide, or mixtures thereof. Dimethylformamide is preferred. Ambient conditions are used. A mild cleaving agent is added to convert one ester linkage to the isolated carboxyl group while retaining the t-butyl ester groupings on the N-acetic acid portions of the structure. Sodium thiosulfate is a preferred cleavage agent.

Step I

The reaction mixture is heated between about 90° and 100° C. for between about 0.5 and 6 hr (preferably about 2 hr) followed by cooling to ambient temperature. The reaction product is diluted with about a volume equivalent of a dipolar aprotic water-immiscible hydrocarbon solvent. Hydrocarbon or aromatic compounds (e.g. toluene) are preferred.

Step J

The organic solvent phase of step I is contacted at least once with an aqueous buffer having a pH of between about 1 and 4. A suitable buffer is 0.1M phosphate having a pH of about 2. The aqueous phase and organic phases are separated, and the organic phase is removed, e.g. under reduced pressure, producing crude compound 3.

Step K

The crude product 3 of Step J is purified, e.g. use of column chromatography (e.g. regular or revenue phase)

which is conventional in the art. The solid phase can be for example, silica gel or alumina. The eluent is a mixture of organic alkyl hydrocarbon and an organic alkyl ester (e.g., n-hexane/ethyl acetate) using increasing solvent polarity. The product is removed from the column using an aqueous weak organic acid and organic alkyl ester, preferably, aqueous acetic acid in ethyl acetate.

The structure of purified compound (e.g. 3) is consistent using various spectral analyses.

Step L

The purified product of step J is dissolved in a chlorinated hydrocarbon solvent (e.g. dichloromethane, dichloroethane, trichloroethane, tetrachloroethane, methylchloroform, chloroform or mixtures thereof and carboxyl activating group, e.g., 1-hydroxybenzotriazole in a dipolar aprotic solvent (e.g. dimethylformamide). The solution is next mixed with a peptide coupling agent, e.g. dicyclohexylcarbodiimide in a chlorinated hydrocarbon solvent at about 0° C. for 0.5 to 4 hr, then at ambient temperature for 0.5 to 6 hr and filtered. Preferably, the solution is stirred at about 0° C. for 1 hr, followed by ambient temperature for 2 hr and filtered. The filtrate is evaporated to dryness (reduced pressure) and the activated ester is dissolved in a dipolar aprotic solvent, e.g. dimethylformamide, and a chlorinated hydrocarbon, e.g. dichloromethane.

Step M (a) peptide synthesis agent

The activated ester of Step L is contacted with stirring with a N-α-Fmoc-protected amino acid, e.g. N-α-Fmoc lysine, partially dissolved in a polar aprotic water-immiscible hydrocarbon solvent (e.g. ethylene glycol monomethyl ether). Additional trialkylamine (e.g. diisopropylethylamine) is added to adjust the pH to about 7–9. The resulting solution is stirred at ambient temperature for between about 6 and 48 hr. Preferably the pH is about 8, and the time is about 20 to 24 hr. The solvents are removed using reduced pressure.

b. MRI contrast agent

In another aspect the product of Step L is contacted by stirring with a protected amino acid of the structure: A—NH—CH—(COOR)—Q—NH$_2$ wherein A and Q are defined hereinabove. Step M(a) is then generally followed or adapted.

Step N

The residue of Step M(a) or Step M(b) is dissolved in an organic alkyl ester (e.g. ethyl acetate) and excess protected amino acid (e.g. N-α Fmoc amino acid) is extracted using aqueous weak organic polyacid (e.g. 10% aqueous citric acid). The organic phase is dried (e.g. molecular sieves), and the solvent is removed using reduced pressure.

Step O

The crude product of Step N (a or b) is purified usually by chromatography. A preferred method is to use a C18 reverse phase column, having an eluent of about 75% acetonitrile/water with 0.1% aqueous trifluoroacetic acid. The structure of the product is confirmed using conventional spectral analysis.

In preferred embodiments for peptide synthesis the amine protecting group A is independently selected from A$^1$ or A$^2$ wherein A$^2$ is independently selected from generally conventional amine protecting agents known to be useful in solid phase peptide synthesis except t-Boc.

The following Examples are provided to be exemplary and illustrative only. They are not to be construed to be limiting in any way.

EXAMPLE NO. 1

SYNTHESIS OF COMPOUND 4

(a) The tetrabutyl ester of the EDTA derivative was synthesized in two steps as shown in Scheme I in FIG. 1.

The starting material 1 (5.0 g) was dissolved in 100 Ml of acetonitrile and mixed with 5 equivalents of tert-butyl bromoacetate and diisopropylethylamine. The reaction mixture was refluxed for 22 hours, cooled, and the solvent was removed under reduced pressure. The residue was triturated with 350 Ml of anhydrous ether stirred overnight and filtered. The filtrate was dried, dissolved in 200 Ml toluene and washed five times with 0.1M phosphate buffer, pH 2.0. The organic phase was dried over molecular sieves and the solvent evaporated under reduced pressure (crude residue, 30.8 g).

(b) The intermediate compound 2 (30.08 g) was dissolved in 200 Ml of DMF, and 4.65 g of sodium thiophenoxide was added. (See Ref. 7 and 11). The reaction mixture was heated at 100° C. for 2 h. cooled to room temperature, and diluted with 300 Ml toluene. After washing with 0.1M phosphate buffer at pH 2.0, the solvent was removed on a rotary evaporator (yellow colored oily residue, 28.18 g). The residue (1.0 g) was loaded on a silica gel column and eluted with 50 Ml fractions of increasing polarity (n-hexane and ethyl acetate). The desired product 3 was eluted with 1% (v/v) glacial acetic acid in ethyl acetate to produce a yellow oily residue, 0.28 g.

$^1$H NMR (500 Mhz, CDCl$_3$)δ3.7 (t,J=7.4, 1H), 3.5 (m, 8H), 3.1 (d, J=7.4, 2H), 1.5 (s, 36H).

Infrared Spectrum (IR) 1730 cm$^{-1}$ (C=O, s).

MS (FAB) calculated M+H for C$_{27}$H$_{49}$N$_2$O$_{10}$=561, observed M+H 561. TLC (SiO$_2$, chloroform/methanol/acetic acid, 9:1:0.004) R$_f$ 0.52.

(c) The final compound 4 (FIG. 1) was prepared by using HOBt (1-hydroxybenzotriazole) active ester of protected EDTA (3), (as adapted from Ref. 12). The tetrabutyl ester of EDTA (0.5 mmol) was dissolved in 3 Ml of dichloromethane and 0.5 mmol of HOBt (dissolved in 1.5 Ml of DMF) was added. The resulting solution was mixed with 0.5 mmol dicyclohexylcarbodiimide (DCC) dissolved in 1 Ml methylene chloride. The reaction mixture was stirred at 0° C. for 1 h, and at room temperature for 2 h, followed by filtration. The filtrate was evaporated to dryness, and the activated ester was dissolved in 5 Ml DMF and 2 Ml methylene chloride. N-α-Fmoc-lysine (0.6 mmol) was partially dissolved in 50 Ml ethylene glycol monoethyl ether and added to the activated ester solution, followed by addition of 100 μL of diisopropylethylamine to bring the apparent pH to 8.0. The reaction was carried out overnight at ambient temperature with constant stirring. The reaction was stopped by removing the solvent under reduced pressure. The residue was taken up in ethyl acetate and excess N-α-Fmoc-lysine was extracted with 10% aqueous citric acid. The organic phase was dried over molecular sieves and the solvent removed under reduced pressure to provide 90% of compound 4 as a dark yellow oil.

$^1$H NMR (500 Mhz, CDCl$_3$) δ7.7 (d,J=7.3, 2H, aromatic), 7.6 (d, J=7.2, 2H, aromatic) , 7.3 (m, 4H, aromatic) , 4.1 (dd, J=4.9, 8.9, 1H), 3.8 (t, J=7.4, 2H), 3.6 (m, 8H), 3.2 (d, J=7.4, 2H), 2.7 (m, 2H), 1.4–1.9 (m, 6H), 1.6 (s, 36H).

IR spectrum 1730 cm$^{-1}$ (C=O,s).

Ms (FAB) calculated M+H for C$_{48}$H$_{71}$N$_4$O$_{13}$=911, observed M+H 911. TLC (SiO$_2$, acetone/water, 7:3), R$_f$ 0.77.

EXAMPLE 2

SYNTHESIS OF COMPOUNDS RELATED TO COMPOUND 4

(a) Similarly, when compound 1 in Example 1 is replaced with a stoichiometrically equivalent amount of

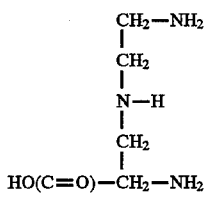

the corresponding DTPA structure is obtained when step 1(b), 1(c) and 1(d) are repeated.

EXAMPLE 3

Formation of Metal Ion Ligand Chelate (a) MRI

The product of Example 1 is contacted with aqueous trifluoroacetic acid at ambient temperature for 2 to 6 hr which removes all t-butyl groups creating the free carboxyl groups ligand.

Fmoc is then removed with mild dilute aqueous base (such as 0.1N sodium hydroxide) at ambient temperature for 10 to 30 min.

Contacting the free carboxyl chelate with aqueous metal ion salts such as iron sulfate, gadolinium chloride and the metal ion chelate is isolated using ion exchange or reverse phase high performance liquid chromatography.

These complexes are useful for MRI.

EXAMPLE 4

Solid Phase Polypeptide Synthesis

The Merrifield solid phase synthesis of polypeptides is conventional in the peptide art. See Ref. 9, and U.S. Pat. No. 3,531,258. For more recent solid/phase synthesis using modified amino acid derivatives, see J. Nestor, et al. U.S. Pat. No. 4,318,905. The procedures in this U.S. patent can be adapted for the present process.

(a) A conventional solid phase polypeptide synthesizer is used to form a polypeptide chain. The chain is contacted piperidine to produce the terminal free amine. The Fmoc, tetra t-butyl ester formed in Example 1, having one free carboxyl group in dichloromethane is contacted with HBOT in DMF and DCC and introduced into the synthesizer forming the peptide bond.

The Fmoc is cleaved using piperidine in dichloromethane. The free amine is available for coupling with the next protected amino acid. Any number of amino acids may be used.

The solid phase is then treated with aqueous trifluoroacetic acid (80%) for 6 to 8 hr at ambient temperature. The free polypeptide (free carboxylate chelate) is precipitated with t-butyl methyl ether. This polypeptide can be further purified using HPLC.

The metal ion chelate is formed by contact with aqueous metal salts as described in U.S. Pat. No. 4,647,447.

EXAMPLE 5

Administration of MRI Agent

The administration route and concentration dose of the compounds of the present invention as MRI agents is determined by the physician involved with the MRI. See especially Grise, et al. U.S. Pat. No. 4,647,447 for the metal ion—ligand chelate useful as an MRI agent.

While only a few embodiments of the invention have been shown and described herein, it will become apparent to those skilled in the art that various modifications and changes can be made in the synthesis of metal ion-containing amino acid chelates useful as MRI contrast enhancing agents or for use in solid phase peptide synthesis without departing from the spirit and scope of the present invention. All such modifications and changes coming within the scope of the appended claims are intended to be carried out thereby.

We claim:

1. An amine protected amino acid-chelate, which is useful as an unnatural amino acid to replace a natural amino acid in the solid phase synthesis of a peptide as a precursor to introduce said unnatural amino acid, which unnatural amino acid is capable of binding a metal atom as a chelate in the peptide chain, said amino acid-chelate hayinc the structure:

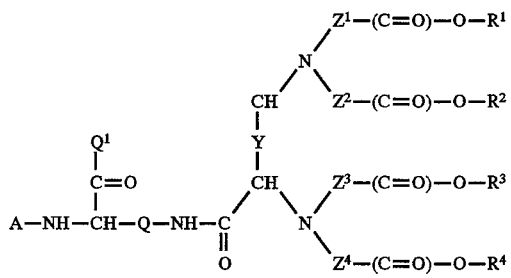

wherein Y is a direct bond,

A is the amine protecting group 9-fluorenylmethylcarbonate (Fmoc);

$Q$ is selected from a straight chain alkylene, or a branched chain alkylene, having 1 to 10 carbon atoms;

$Q^1$ is —OH;

$Z^1$, $Z^2$, $Z^3$, and $Z^4$ are identical and selected from —$CH_2$—, or —$CH_2CH_2$—;

$R^1$, $R^2$, $R^3$, and $R^4$ are identical and selected from —H, or —$C(CH_3)_3$.

2. The amino acid-chelate of claim 1 wherein $Z^1$, $Z^2$, $Z^3$, and $Z^4$ are each —$CH_2$—.

3. The amino acid-chelate of claim 1 wherein Q is the straight chain alkylene —$CH_2CH_2CH_2CH_2$—, and $Z^1$, $Z^2$, $Z^3$ and $Z^4$ are each —$CH_2$—.

4. The amino acid-chelate of claim 1 wherein Q is the straight chain alkylene —$CH_2CH_2CH_2$—.

5. The amino acid-chelate of claim 4 wherein $Z^1$ to $Z^4$ are each —$CH_2CH_2$—.

6. The amino acid chelate of claim 1 wherein $R^1$, $R^2$, $R^3$, and $R^4$ are each —H.

7. The amino acid chelate of claim 6 wherein $Z^1$, $Z^2$, $Z^3$, $Z^4$ are each —$CH_2$—.

8. The amino acid chelate of claim 4 wherein $Z^1$, $Z^2$, $Z^3$, and $Z^4$ are each —$CH_2$—.

9. The amino acid chelate of claim 1 wherein Q is a branched chain alkylene.

10. The amino acid chelate of claim 9 wherein $R_1$ to $R_4$ are each —$C(CH_3)_3$.

11. The amino acid chelate of claim 9 where $R^1$ to $R^4$ are each —H.

12. The amino acid chelate of claim 9 wherein $Z^1$ to $Z^4$ are each —$CH_2$—.

13. The amino acid chelate of claim 9 wherein $Z^1$ to $Z^4$ are each —$CH_2CH_2CH_2CH_2$—.

* * * * *